United States Patent [19]
Chiesi et al.

[11] Patent Number: 6,103,760
[45] Date of Patent: Aug. 15, 2000

[54] AMINOTETRALIN DERIVATIVE FOR THE THERAPY OF CARDIOVASCULAR DISEASES

[75] Inventors: Paolo Chiesi; Stefano Bongrani; Roberta Razzetti; Maurizio Civelli; Alberto Umile, all of Parma, Italy

[73] Assignee: Chiesi Farmaceuticals S.p.A., Parma, Italy

[21] Appl. No.: 09/328,434

[22] Filed: Jun. 9, 1999

Related U.S. Application Data

[63] Continuation-in-part of application No. 08/913,363, filed as application No. PCT/EP96/01060, Mar. 13, 1996.
[51] Int. Cl.$^7$ .......................... A61K 31/21; A61K 31/135
[52] U.S. Cl. ............................................. 514/510; 514/657
[58] Field of Search ...................... 514/657, 510

[56] References Cited

U.S. PATENT DOCUMENTS 4,134,997  1/1979  Cannon et al. .................. 424/330

OTHER PUBLICATIONS

Carine Morisoco et al, "Hemodynamic Effects of Graded Oral Doses of a New Dopaminergic Analogue CHF 1035 in Patients with Congestive Heart Failure", Special Issue, Journal of the American College of Cardiology, Feb. 1995.

Enrico Redenti et al, Application of γ–Cyclodextrin to Enantiomeric Purity Determination of a New 2–Amino–Tetralin Derivative γ $^1$H–NMR Spectroscopy, Chirality 4:404–405 (1992).

*Primary Examiner*—Phyllis G. Spivack
*Attorney, Agent, or Firm*—Oblon, Spivak, McClelland, Maier & Neustadt, P.C.

[57] ABSTRACT

Left ventricular dysfunction is treated by a process, comprising:

administering to a subject suffering from left ventricular remodeling a therapeutically effective amount of 5,6-dihydroxy-2-methylaminotetralin, or 5,6-diisobutyroyl-oxy-2-methyl-aminotetralin, or a pharmaceutically acceptable salt thereof in combination with an angiotensin-converting enzyme inhibitor.

3 Claims, No Drawings

AMINOTETRALIN DERIVATIVE FOR THE THERAPY OF CARDIOVASCULAR DISEASES

CROSS-REFERENCE TO RELATED APPLICATIONS

This application is a continuation-in-part of U.S. application Ser. No. 08/913,363, filed Oct. 14, 1997, which is a 371 of PCT/EP96/01060 filed Mar. 13, 1996, a Continued Prosecution Application (CPA) of which was filed on Feb. 4, 1999.

BACKGROUND OF THE INVENTION

1. Field of the Invention

The present invention relates to the use of 5,6-diisobutyroyloxy-2-methylaminotetralin in the preparation of pharmaceutical compositions for the therapy of cardiac disorders, particularly congestive heart failure.

2. Discussion of the Background

Notwithstanding the therapeutical progresses of the last years, congestive heart failure is still one of the main death causes.

The symptomatic therapy usually aims at reducing the workload of the decompensed heart and improving the mechanical function.

Recently, cardiac failure has been proved to be related to important biochemical and neurohumoral changes involving different factors.

In fact, when cardiac output diminishes, compensatory mechanisms act in the body in order to maintain the circulatory homeostasis.

In heart failure, vasoconstriction associated with the activation of said mechanisms cause an increase in peripheral vascular resistance.

As a consequence, the after-load increases which can in turn further strain the already weakened heart, triggering a vicious circle which leads to a progress of the pathology.

This generalized vasoconstriction is mainly caused by the activation of the sympathetic nervous system consequent to the increase of plasma catecholamnines, particularly adrenalin, which is an early signal of cardiac decompensation.

A close relationship between degree of sympathetic activation and severity of the disease seems to exist, and a direct connection between noradrenaline plasmatic levels and mortality seems moreover established.

Therefore, the therapy of congestive heart failure has to be directed to the improvement of the hemodynamic factors, on one hand, and to the pharmacological modulation of the neurohumoral system on the other.

Dopaminergic drugs appear as candidates to become established as drugs for heart failure in the majority of patients.

In particular, dopamine has peculiar characteristics, compared with the other medicaments, since it stimulates both dopaminergic and alpha and beta-adrenergic receptors.

Two types of dopaminergic receptors exist: those located on the smooth muscle of the vascular system ($DA_1$ receptors) which mediate vasodilation in the renal, mesenteric, cerebral and coronary districts, and those in pre-synaptic position ($DA_2$ receptors), which inhibit noradrenaline release from post-ganglionic sympathetic nerve endings to blood vessels and heart.

The usefulness of dopamine in the treatment of heart failure is, however, restricted by it being inactive orally.

Analogously dobutamine, a synthetic analogue of dopamine, can be used only intravenously.

Aminotetralin derivatives have been studied for a long time as dopamine structural analogues for any uses as medicaments.

However, none of these compounds has up to now been introduced in therapy.

One of them, 5,6-dihydroxy-2-methylaminotetralin hydrobromide, is disclosed as a coronary vasodilator in U.S. Pat. No. 4,134,997 in the name of Joseph G. Cannon.

Cannon administered the compound to dogs at a rate of approximately 10 µg/kg animal weight per minute (range 8.5–13.9) by a continuous intravenous infusion and demonstrated a substantial increase in coronary blood flow.

5,6-Diisobutyroyloxy-2-methylaminotetralin, hereinafter referred to as CHF 1035, has been described first in GB Pat. 2123410 among a series of aminotetralin derivatives disclosed as potential antibronchospastic due to their activity on adrenergic receptors.

Both 5,6-dihydroxy-2-methylaminotetralin (hereinafter indicated with the experimental abbreviation CHF 1024) and CHF 1035 have been formerly characterized as compounds having prevailing selective activity on $\beta_2$ adrenergic receptors.

Now it has been surprisingly found that CHF 1024 and CHF 1035, in addition to the already known $\beta_2$ agonist activity, have remarkable peripheral $DA_2$ and $\alpha_2$ presynaptic activities leading to a reduction of the sympathetic tone, which is elevated in heart failure patients.

Studies carried out in the animal proved that CHF 1024 and CHF 1035 have a vasodilating activity due the combination of their effects on $\alpha_2$ and $\beta_2$ and $DA_1/DA_2$ receptors as well as a cardiac isotropic activity.

They are effective at a very low doses, even by oral route.

The peripheral $\alpha_2$ adrenergic and peripheral $DA_2$ dopaminergic activities of the aminotetralin derivatives of the present invention have never been described until now.

On the contrary, it was previously affirmed by Hilditch A. and Drew G. M. in *European Journal of Pharmacology* vol. 72, pages 287–296, 1981 that the compound 5,6-dihydroxy-2-methylaminotetralin was inactive as dopamine receptor agonist in relaxing splenic artery strips.

We have demonstrated that both CHF 1024 and CHF 1035 have agonist activity on dopaminergic receptors and that they are selective for the presynaptic $DA_2$ ones.

The $\alpha_2$ adrenergic and $DA_2$-dopaminergic activities of the compounds have been evaluated in binding tests (example 1 and 3), in isolated neuronally-stimulated rat vas deferens (example 2) and in rabbit rectococcygeus muscle (example 4).

The cardiovascular effects of the compounds have been evaluated in vivo in anesthetized rats both after intravenous and intraduodenal administration (example 5).

EXAMPLE 1

The affinity of CHF 1024 and CHF 1035 for $\alpha_2$, adrenergic receptors was tested on human platelets and on rat cerebral cortex.

The antagonist [3H]-rauwolscine was used as marker of the receptor, being its binding reversible, saturable and specific.

CHF 1024 exhibited a significantly higher affinity than dopamine, 9 times in platelets and 15 times in cerebral cortex. The affinity of CHF 1035 was similar to that of dopamine, utilized as reference compound.

The lower affinity of CHF 1035 for the receptor is probably due to the esterification of the molecule.

|  | CHF 1024 | CHF 1035 | DOPAMINE |
|---|---|---|---|
| human platelets | $3.39 \times 10^{-7}$ ($\pm 0.13$) | $2.70 \times 10^{-5}$ ($\pm 0.45$) | $3.04 \times 10^{-6}$ ($\pm 0.38$) |
| rat cerebral cortex | $2.62 \times 10^{-7}$ ($\pm 0.58$) | $2.65 \times 10^{-6}$ ($\pm 0.67$) | $4.06 \times 10^{-6}$ ($\pm 0.97$) |

Values are expressed as $IC_{50}$ = molar concentration of drug required for 50% inhibition of [$^3$H]-rauwolscine specific binding.

EXAMPLE 2

The $\alpha_2$-adrenergic activity of the aminotetralin derivatives CHF 1024 and CHF 1035 has been evaluated in isolated neuronally-stimulated rat vas deferens in comparison with dopamine.

The results are expressed in the following table as $IC_{50}$ value=molar concentration of drug which induces 50% inhibition of the electrically induced contraction:

|  | CHF 1024 | CHF 1035 | DOPAMINE |
|---|---|---|---|
| $IC_{50}$ (M) | $2.70 \times 10^{-7}$ | $7.14 \times 10^{-8}$ | $4.91 \times 10^{-6}$ |
| C.I. | 2.15–3.38 | 5.63–9.05 | 4.19–5.75 |

C.I. = 95% Confidence Interval

The compounds CHF 1024 and CHF 1035 are about 20–70 times more potent than dopamine, respectively.

EXAMPLE 3 —peripheral $DA_2$ dopaminergic activity (binding test)

The affinity of CHF 1024 for peripheral $DA_2$ dopaminergic receptors was tested on bovine adrenal cortex evaluating its effect on the interaction of [$^3$H](−)sulpiride with the specific binding sites of this system.

Dopamine has been employed as reference compound.

The results, expressed as $IC_{50}$ (molar concentration required for 50% inhibition of specific binding) are reported here below.

|  | CHF 1024 | DOPAMINE |
|---|---|---|
| Bovine adrenal cortex [$^3$H]-sulpiride | $2.1 \times 10^{-8}$ | $2.3 \times 10^{-7}$ |

The affinity of CHF 1024 for $DA_2$ receptors is 11 times higher than that of dopamine.

EXAMPLE 4 —peripheral $DA_2$ dopaminergic activity (in vitro test)

The activity of CHF 1024 and CHF 1035 on peripheral $DA_2$ dopaminergic receptors has been tested in the electrically stimulated rabbit rectococcygeus muscle.

Both compounds determined a dose-dependent inhibition of contraction induced by electrical stimulation and were approximately 3 times more potent than dopamine, utilized as reference compound.

In the table below the $IC_{50}$ values (molar concentration of drug which induces 50% inhibition of the electrically induced contraction) are reported:

|  | CHF 1024 | CHF 1035 | DOPAMINE |
|---|---|---|---|
| $IC_{50}$ (M) | $3.73 \times 10^{-8}$ | $2.96 \times 10^{-8}$ | $9.93 \times 10^{-8}$ |
| C.I. | 3.16–4.36 | 2.14–3.88 | 4.79–18.21 |

(95% Confidence Interval)

The effects produced by CHF 1024, CHF 1035 and dopamine were competitively antagonized by the selective $DA_2$-antagonist domperidone.

EXAMPLE 5 —In viva cardiovascular effects

Male albino rats (Sprague Dawley, 350–400 g) were anesthetized by sodium pentobarbital (60 mg/kg) and maintained by i.v. infusion (6 mg/h). The trachea was cannulated to facilitate spontaneous respiration and body temperature was maintained at 37° C. Homoiothermic Blanket Control System (Harvard, England).

The right femoral artery was cannulated for arterial blood pressure measurement and left jugular vein or duodenum were cannulated for drug administration. Mean arterial pressure and heart rate were continuously monitored by pressure transducer and medium gain amplifier triggered by the ECG signal, respectively.

After a stabilization period of about 15 min, CHF 1024 (0.23, 0.69 and 2.3 µg/kg/min) was administered by intravenous infusion for 30 min and cardiovascular parameters were recorded for further 30 min after discontinuation.

CHF 1035 was administered intraduodenally (1 mg/kg).

The response to CHF 1035 was determined in the absence and in the presence of the selective $\beta_2$-adrenoceptor antagonist ICI 118.551 (0.2 mg/kg i.v.) and the selective $DA_2$-dopaminergic antagonist domperidone (0.3 mg/kg i.v.) both alone and in combination. The antagonists were administered 10 min before the i.d. drug administration.

Intravenous administration of CHF 1024 induced a dose-dependent reduction in mean parterial pressure which persists even after infusion discontinuation.

Effects induced by intravenous infusion of the compound on mean arterial pressure in anesthetized rat. Mean ±s.e.m. values (expressed as changes from basal value) are reported.

| | | Vehicle CHF 1024 | | | |
|---|---|---|---|---|---|
| pg/kg/min | | min after infusion start | | min after infusion stop | |
| i.v. | n | 5 | 30 | 5 | 30 |
| — | 7 | 1.7 ± 2.0 | 3.7 ± 2.9 | 4.0 ± 2.2 | 2.0 ± 2.4 |
| 0.23 | 6 | −6.3 ± 2.1 | −13.7 ± 4.2 | −8.3 ± 3.4 | −8.0 ± 3.3 |
| 0.69 | 6 | −24.0 ± 3.8 | −25.7 ± 5.4 | −12.7 ± S.2 | −6.7 ± 3.3 |
| 2.3 | 6 | −47.7 ± 7.4 | −48.7 ± 5.7 | −34.0 ± 6.3 | −25.3 ± 7.1 | n = number of animals

In spite of marked hypotension, no increase in heart rate was observed.

Analogously, intraduodenal administration of CHF 1035 at 1 mg/kg markedly reduced blood pressure without affecting heart rate.

The hypotensive response was characterized by a rapid and marked fall (peak effect of about 45% reduction from basal value at 5 min after administration) followed by a slow recovery (about 20% reduction from basal value is still present 2 hours after administration).

It has been shown that the peak effect is significantly reduced by pretreatment with the $\beta_2$-antagonist, while $DA_2$-antagonist significantly shortened the hypotensive response (the basal value is completely recovered 60 min from administration). The administration of both antagonists combined completely abolished the hypotensive response.

It has been so demonstrated that the compound is active at doses considerably lower than those described by Cannon and that both $\beta_2$-adrenergic and $DA_2$-doparninergic receptors are involved in the hypotensive activity.

In particular the $DA_2$ stimulation seems to be responsible of the long-lasting activity of the compound.

In order to investigate the effects of the compound both on the hemodynamic parameters and the neurohumoral pattern, a randomized double-blind study versus placebo was carried out in 18 patients with a moderate congestive heart failure (class NYHA II–III).

Each patient received on 3 consecutive days 2 active doses of CHF 1035 and 1 placebo dose.

The following hemodynamic parameters were evaluated:

pulmonary capillary wedge pressure (PCWP) (mmHg);

cardiac index (CJ) (L/min/m$^2$);

stroke volume index (SVI) (ml/min/m$^2$);

systemic vascular resistance (SVR) (dyneseccm$^{-5}$);

heart rate (HR) (bpm);

mean blood pressure (BPm) (mmHg).

The evaluations were carried out by catheterization of the right heart (Swan-Ganz catheter), measuring the hemodynamic parameters of the tested medicament before administration or "pre-dose" (PD) and for the 300 subsequent minutes after the administration or "after-dose" (AD), every 20 minutes for the first 2 hours, then every 60 minutes.

To evaluate the effects of the compound on neurohormones, noradrenaline (NE) (pg/ml) and adrenalin (E) (pg/ml) plasmatic levels were further evaluated, before and 140 minutes after the administration of CHF 1035 and placebo, respectively The administration of CHF 1035 at the 3 dose levels, induced changes in the hemodynamic and neurohumoral parameters as shown in the following table:

−35.2% for the 3 dose levels), only a relative increase in heart rate occurs, which is not clinically significant.

The reduction in ventricular after-load, which is the expression of the decrease in the peripheral vascular resistances, induces a significant increase in the cardiac index.

Moreover the significant reduction in the pulmonary capillary wedge pressure should be stressed, which means that the medicament also induces venous vasodilation, with a consequent reduction in the left ventricle preload.

Therefore, the general hemodynamic effect CHF 1035 can be ascribed to the peripheral vasodilating activity of the medicament, both arterial and venous.

This evident activity on peripheral receptors could have induced a neurohumoral hyper-reactivity, with a consequent increase in noradrenaline and adrenalin plasmatic levels, which is an undesired reaction in a pathological subject.

On the contrary, the results reported above prove that CHF 1035 is capable of inducing systemic vasodilation without inducing any reflected increase in catecholamines plasmatic levels.

The vasodilating activity of the compound derives from its receptor properties, particularly from the activity on pre-synaptic $DA_2$ and $\alpha_2$ receptors, the stimulation of which can inhibit the catecholamine release, as it is well known.

As said before, congestive heart failure is one of the most common causes of death and disability in industrialized nations and is among the syndromes most commonly encountered in clinical practice, affecting nearly 4 million persons in the USA and 14 million individuals in Europe.

The current pharmacological treatment of the condition includes diuretics, angiotensin converting enzyme (ACE) inhibitors and digitalis.

There is a strong impression among the experts that the pharmacologic treatment of patients with heart failure remains suboptimal and more effective treatment is required to prevent complications and thereby reduce morbidity and mortality.

It has been demonstrated that CHF 1035 improves the clinical condition and the exercise capacity of patients with congestive heart failure when used as add-on therapy to baseline therapy with diuretics or with diuretics and ACE-inhibitors and/or with diuretics and digitalis.

|  | 5 mg | | 10 mg | | 15 mg | |
| --- | --- | --- | --- | --- | --- | --- |
|  | PD | AD | PD | AD | PD | AD |
| PCWP | 22 ± 5 | 18 ± 4* | 20 ± 6 | 16 ± 9* | 21 ± 7 | 16 ± 6* |
| CI | 3 ± 1 | 3.4 ± 1* | 2.7 ± 1 | 3.4 ± 1* | 3 ± 1 | 4 ± 1* |
| SVI | 139 ± 12 | 43 ± 11 | 38 ± 7 | 45 ± 10* | 40 ± 10 | 49 ± 11* |
| SVR | 1243 ± 27 | 1052 ± 265* | 1382 ± 45 | 1009 ± 315* | 1359 ± 36 | 881 ± 257* |
| HR | 74 ± 11 | 78 ± 11 | 70 ± 11 | 76 ± 12 | 74 ± 12 | 80 ± 10* |
| BPm | 85 ± 12 | 82 ± 12 | 85 ± 10 | 77 ± 13* | 87 ± 11 | 79 ± 12* |
| NE | 299 ± 135 | 301 ± 156 | 285 ± 244 | 244 ± 88* | 340 ± 162 | 308 ± 133 |
| E | 56 ± 29 | 42 ± 21* | 65 ± 42 | 62 ± 44 | 53 ± 25 | 58 ± 24 |

*$p < 0.05$

On the contrary, the administration of placebo induced no changes in the same parameters.

The results prove that CHF 1035, at the doses used in the study, induces a significant improvement in hemodynamic parameters and is characterized by a particularly favorable pharmacological profile.

Whilst a dose-related reduction in the peripheral vascular resistances is observed (respectively −15.4%; −27.0%;

It has also been shown that the pharmacodynamic effects last longer than detectable serum levels of the drug. The time course of these effects is independent of the kinetics of the drug in the body.

The effects of CHF 1030 as added therapy have been evaluated in patients suffering from NYHA class II–III congestive heart failure due to mild hypertension, or coronary disease, or chronic cardiomyopathy, who were on diuretics or diuretics and an angiotensin-converting enzyme inhibitor.

Recruited patients were randomly assigned to added double-blind treatment with placebo or with three different doses of the study drug (5 mg, 10 mg, 15 mg).

The study therapy was started by patients on day 1 and proceeded until day 28 of the study.

The following parameters have been considered to determine the clinical condition of patients:
pulmonary congestion;
systemic congestion;
central haemodynamics;
regional blood flows.

The functional response to the treatments has been evaluated by exertional tests, the 6-minute walking test and the 130-meter walking test.

CHF 1035 improved the functional and clinical condition of patients, compared to placebo.

This improvement was ostensible in terms of the NYHA functional class, exercise performance, and symptoms and signs of pulmonary and systemic congestion, central haemodynamic alterations, and decreased regional/organ blood flows.

For the evaluation of clinical condition, more than 60 symptoms or signs were evaluated.

For statistical purposes scores from signs and symptoms (as applicable) were summed to form clinical compound scorings (CCSs) of pathophysiological importance in congestive heart failure.

Three CCSs were evaluated by adding the scores for certain symptoms and signs; each symptom and sign was used for only one CCS. The central hemodynarnics (CH, 0–17), the pulmonary congestion (PC, 0–26), and the systemic congestion (SC, 0–8) CCS were associated with the NYHA functional class ($p=0.013$; $p=0.001$; $p=0.001$) before, and they correlated with it positively ($p=0.001$; $p=0.022$; $p<0.001$) after CHF 1035 add-on therapy.

The pulmonary congestion CCS correlated also with the 130-m mean walking velocity ($p=0.002/p=0.035$) and with the left ventricle end-diastolic ($p=0.026/p=0.019$) and end-systolic internal dimensions before/after CHF 1035 add-on therapy.

The pulmonary congestion appeared as the most important determinant of the functional status in congestive heart failure and was the most sensitive CCS to CHF 1035 add-on therapy.

Furthermore, pharmacological and clinic pharmacological studies showed that CHF 1035 increases diuresis without affecting natriuresis and kaliuresis.

CHF 1035 is the diisobutyroyl ester of 5,6-dihydroxy-2-methylaminotetralin, which is referred to as CHF 1024.

Immediately after the administration, CHF 1035 is transformed by the plasma and tissue esterases into the pharmacologically active desesterified form, which is also included within the present invention.

Due to these favorable characteristics, CHF 1035 can be advantageously used as pro-drug for the preparation of pharmaceutical compositions for the therapy of cardiac disorders and in particular for congestive cardiac failure.

The daily dose of the active ingredient can vary from 1–100 mg and preferably ranges from 2.5–20 mg.

The administration can be performed by any route, preferably by the oral route.

For oral administration, the compound can be formulated in solid or liquid preparations, preferably in tablets, using the additives and excipients of common use in pharmaceutical technique.

Another particularly advantageous method for the administration of the compound of the invention are the transdermal systems, which are adhesive matrixes that can be applied to the skin containing a suitable concentration of the active ingredient, which can gradually be released thus entering the blood circulation.

Effects of CHF 1024 in combination with an ACE inhibitor on adrenergic activity and left ventricular remodeling in an experimental model of left ventricular dysfuiction after coronary artery occlusion.

Left ventricular remodeling after infarction involves progressive dilatation of the chamber, hypertrophy of the surviving myocytes, rearrangement of the extracellular matrix and neurohumoral activation. Drugs that influence the neurohumoral response, particularly angiotensin-converting enzyme inhibitors (ACEi) have beneficial effects in the treatment of myocardial infarction and congestive heart failure. Actually ACE inhibition is now a recommended therapy in patients with congestive heart failure. Since CHF 1024 has been shown to reduce sympathetic hyperactivity (1), we verify that the drug might provide additional benefit with ACE inhibition in a rat model of left ventricular dysfunction (LVD).

The purpose of this study was, therefore: 1 ) to investigate the effects of a four-week infusion of CHF 1024 on morphological, hemodynamic and neurohumoral variables in rats with left ventricular dysfunction receiving an ACEi, and 2) to compare these effects with a four-week treatment with ACEi alone.

As ACEi was employed in the study delapril.

Myocardial infarction (MI) was induced by left coronary artery ligation in 134 rats, and 6 were left unoperated. After two months, the survived animals with ECG evidence of MI entered a four-week treatment phase. They were randomly allocated to one of the following treatments: 1) delapril 6 mg.kg$^{-1}$.day$^{-1}$, (n=12), 2) delapril 6 mg.kg$^{-1}$.day$^{-1}$ and CHF 1024 0.33 mg.kg$^{-1}$.day$^{-1}$ (n=13), 3) vehicle (0.05% ascorbic acid; n=12).

Delapril was dissolved in drinking water at the final concentration of 0.043 mg/ml. The delapril solutions were prepared freshly every third day and their concentration adjusted to body weight every 15 days to obtain an average dose of 6 mg·kg$^{-1}$·day$^{-1}$.

CHF 1024 was administered continuously for four weeks through osmotic minipumps implanted subcutaneously behind the neck.

Concentrated solutions of CHF 1024 were dissolved in 10% ascorbic acid in distilled water at a final concentration of 40 mM (mean delivery rate 0.33 mg·kg$^{-1}$·day$^{-1}$).

At week 4 of treatment, the rats were placed in individual metabolic cages to collect 24-hour urine for measuring catecholamine excretion. On completion of the treatment phase, the animals were anesthetized with pentobarbital 50 mg/kg i.p. A microtip pressure transducer was inserted into the right carotid artery to record systolic and diastolic blood pressure (SBP, DBP), and advanced into the left ventricle for measurement of LV pressures. The heart was then arrested in diastole for LV histomorphometry. Only rats with mean infarct size 24 12%, histologically determined in 6–10 serial cross-sections as percentage of LV area, were analyzed. The numbers of animals analyzed in each experimental group were 6 (vehicle), 6 (delapril alone), 8 (delapril and CHF 1024) and 6 non-operated.

Urine norepinephrine excretion was unaffected by delapril alone, but was reduced by the addition of CHF 1024 (40% with respect to the vehicle group).

Morphometric bidimensional and three-dimensional analyzes of the LV were done according to a method previously described (1) and ampliated for three-dimensional evaluations (2).

The left ventricular geometry was affected by infarction as reflected by increases in LV chamber radius at the equatorial level (+30%, p=0.005), total LV height (+8%, p=0.047) and by a shift of the LV chamber center ("chamber shift", p<0.001) in the vehicle-infused MI group compared to non-operated animals.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A method of treatment of left ventricular dysfunction, comprising:

administering to a subject suffering from left ventricular remodeling a therapeutically effective amount of 5,6-dihydroxy-2-methylaminotetralin, or 5,6-diisobutyroyl-oxy-2-methyl-aminotetralin, or a pharmaceutically acceptable salt thereof in combination with an angiotensin-converting enzyme inhibitor.

2. The method according to claim 1, wherein said left ventricular remodeling is a consequence of myocardial infarction.

3. The method according to claim 1, wherein the angiotensin converting enzyme inhibitor is delapril.

* * * * *

UNITED STATES PATENT AND TRADEMARK OFFICE
CERTIFICATE OF CORRECTION

PATENT NO. : 6,103,760
DATED : August 15, 2000
INVENTOR(S) : Paolo CHIESI, et al.

It is certified that error appears in the above-identified patent and that said Letters Patent is hereby corrected as shown below:

On the Title Page, Item [30] the Foreign Application Priority Data is missing in the Letters Patent. It should read as follows:

[30]    Foreign Application Priority Data

Mar. 17, 1995    [IT]    Italy ........................... MI95A000532

ALSO --

On the Title Page, Item [73] the Assignee is incorrect. It should read as follows:

[73]    Assignee: Chiesi Farmaceutici S.p.A., Parma, Italy

Signed and Sealed this

First Day of May, 2001

Attest:

NICHOLAS P. GODICI

*Attesting Officer*    *Acting Director of the United States Patent and Trademark Office*